United States Patent
Schramm

[19]

[11] Patent Number: 5,964,526
[45] Date of Patent: Oct. 12, 1999

[54] KNEADER AND RHEOMETRIC ANALYSIS METHOD IN A KNEADER

[75] Inventor: Gebhard Schramm, Karlsruhe, Germany

[73] Assignee: Gebruder Haake GmbH, Karlsruhe, Italy

[21] Appl. No.: 08/953,386

[22] Filed: Oct. 17, 1997

[30] Foreign Application Priority Data

Oct. 28, 1996 [DE] Germany .................. 196 44 681

[51] Int. Cl.⁶ .................. B01F 7/02; B29B 7/28
[52] U.S. Cl. .................. 366/96; 366/140
[58] Field of Search .................. 366/96, 97, 100, 366/140, 142, 292, 297

[56] References Cited

U.S. PATENT DOCUMENTS

| | | | |
|---|---|---|---|
| 3,447,201 | 6/1969 | Seanor et al. | 366/142 |
| 4,443,110 | 4/1984 | Den Otter | 366/97 |
| 4,818,113 | 4/1989 | Patel | 366/142 |
| 4,830,506 | 5/1989 | Borzenski | 366/97 |
| 4,953,984 | 9/1990 | Miyoshi | 366/97 |
| 5,061,078 | 10/1991 | Yada | 366/97 |
| 5,152,609 | 10/1992 | Hader et al. | 366/142 |
| 5,259,670 | 11/1993 | Brown | 366/97 |
| 5,460,445 | 10/1995 | Miyoshi et al. | 366/97 |

FOREIGN PATENT DOCUMENTS

| | | |
|---|---|---|
| 0392787 | 10/1990 | European Pat. Off. |
| 232454 | 1/1986 | Germany. |
| 3734215 | 4/1989 | Germany. |
| 4024863 | 2/1992 | Germany. |

*Primary Examiner*—Tony G. Soohoo
*Attorney, Agent, or Firm*—Antonelli, Terry, Stout & Kraus, LLP

[57] ABSTRACT

A kneader for viscoelastic materials has a kneading chamber constructed in a casing and which contains at least two rotated rotors with which the materials can be kneaded to a viscoelastic mass. In order to be able to determine in a sufficiently precise manner the elastic and viscous parameters of the mass to be kneaded during the kneading process and follow it over time, a test chamber is provided, to which can be supplied from the kneading chamber a test fraction of the mass and use is made of a preferably dynamically measuring rheometer for determining the elastic or viscous parameters of the test fraction of the mass in the test chamber. The inner wall of the kneading chamber is formed sectionwise by an adjustable wall part and the test chamber can be formed by retracting said wall part.

14 Claims, 4 Drawing Sheets

KNEADER AND RHEOMETRIC ANALYSIS METHOD IN A KNEADER

FIELD OF THE INVENTION

The invention relates to a kneader, particularly for viscoelastic materials, with a kneading chamber constructed in a casing in which are located at least two rotors with which materials can be kneaded to a visoelastic mass. The invention also relates to a method for the rheometric analysis or examination of a viscoelastic mass in a kneader.

BACKGROUND OF THE INVENTION

Kneaders or so-called closed mixers have been known for a long time and have a closed, usually elongated kneading chamber, in which are located two parallel oriented rotors which are rotated in opposite directions. As a function of the desired nature and quantity, different components of a mixture, particularly high molecular weight, viscoelastic materials, e.g. polymers or elastomers, are introduced through a filling shaft into the kneading chamber. The components of the mixture are exposed to shear forces in the kneading chamber by means of the rotors, so that they are transformed or kneaded to a very homogeneous, viscoelastic mass.

The processing or flow behaviour of high molecular weight materials such as polymer melts or elastomers is determined by a combination of their viscous and elastic characteristics, an important influence being exerted inter alia by the nature and fractions of the components of the mixture and the quality of the distribution level of all the components. The components can be polymers having different molecular structures or can comprise pulverulent fillers with different particle sizes in a differing particle size distribution.

If e.g. high molecular weight and consequently also highly elastic, fractions of a first component are introduced into a low molecular weight, low viscosity, second component and the components are mixed in a turbulent manner in a kneader with two rotors rotated in opposite directions, theoretically following an adequately long mixing time a constant, relatively high degree of mixing is at least asymptotically reached. However, it has been found that this is not the case if the viscoelastic, first component, due to the action of the rotors, is only briefly expanded and then reverts to its original particle form. In this case it must be ensured that the component fractions during kneading are reduced to the smallest possible size, and the thus formed parts are distributed as homogeneously as possible in the mass. The extent of this homogenization process depends on the geometrical conditions of the kneader used, the chosen processing conditions, e.g. the mass temperature, rotor speed and degree of filling of the kneading chamber, and in particular on the viscous and elastic characteristics or parameters of all the components.

A kneading or thorough mixing by the introduction of relatively high shear forces, both onto the high molecular weight, first component and onto the low molecular weight, second component, is intended to lead to a uniform mastication of both molecular structures, and inter alia the molecular chain length of both polymer components, and consequently the viscosity of the total mass are reduced, and the thorough mixing of all the components is facilitated. However, mastication is often more effective in the case of the low molecular weight, second component than of the high molecular weight, first component, whose fractions "float" in the second component and consequently are not sufficiently strongly subject to the action of the shear forces to bring about the desired breaking up of the molecular chains. Therefore the pronounced elastic characteristics of the first component have a marked influence on the viscoelastic characteristics of the overall mixture.

When kneading or thoroughly mixing different types of components, for the aforementioned reasons it is impossible or difficult to forecast how the viscous and elastic properties of the mixture will change during the kneading process. It is therefore impossible to make a reliable forecast as to the extent by which the processing characteristics of the mixture are changed by the kneading process or what use properties the mass will ultimately have. It is consequently of interest to be able to follow both the viscous and elastic characteristics of a mixture during the kneading process as a function of the processing conditions and the mixing time.

In the case of kneaders it is conventional practice (U.S. Pat. No. 3,447,201, EP 0 392 787 A1) to determine the change to the viscous characteristics, e.g. of a polymer mixture, in that on presetting a constant rotor speed determination takes place of the time pattern of the resistance opposed to the rotors by the mass in the kneading chamber, in that the necessary drive motor power is measured. Particularly in the case of smaller laboratory kneaders it is possible to determine the time change of the torque acting on the drive spindles at a constant rotor speed. In such a case the measured torque is considered to be a viscosity parameter of the mass. Kneading in a kneader presupposes that for obtaining an intense thorough mixing the mass is exposed to a turbulent movement or flow in the kneading chamber. As there is no laminar state in the kneading chamber, as is required for absolute viscosity measurements in rheometers, the viscosity parameter determined from the torque of the drive mechanism only has a relative character and in addition the kneader geometry and other kneading parameters have a significant influence on the magnitude of said parameter or characteristic value. Different types of kneaders and varying test parameters consequently always give different viscosity-proportional torque values for identical samples. For example within the framework of quality control, these relative viscosity parameters acquire significance from comparison with the evaluation of the use characteristics of the end product. However, tests with conventional kneaders are unable to provide information on the elastic characteristics of the investigated viscoelastic masses, although specifically in the case of high molecular weight polymers and elastomers the elastic characteristics are often much more important than the viscous characteristics with regards to processability.

It is known from rheology to determine the elastic characteristics of viscoelastic masses in so-called rotary rheometers, where a sample of the mass is exposed to precisely defined shear conditions. For this purpose a sample of the mass is placed in the gap between a rotor plate and a stator plate. If the rotor plate is moved with a small angular amplitude on applying a sinusoidal, oscillating torque, it is possible to establish whether the sample oscillates in equiphase manner with the preset torque, or whether the deformation of the sample with respect to the preset torque takes place with a phase shift angle $\delta$. A substance is classified as purely elastic if the shift angle $\delta$ is 0°. The substance is classified as purely viscous if the angle $\delta$ is 90°. For an angle $\delta$ between 0 and 90°, the substance is called viscoelastic.

In the case of such dynamic measurements, apart from the phase shift angle $\delta$, determination also takes place of the complex modulus $G^*$, which represents the total resistance of the test mass against the forced deformation. On the basis of the quantities δ and G* by applying known mathematical relationships the storage modulus G', which is proportional to the elasticity, and the loss modulus G", which is proportional to the viscosity, can be determined. With a constant oscillation frequency, the time changes of these dynamic measured quantities can be determined as a consequence of e.g. different mixing intensities. Alternatively the viscoelastic behaviour of the test mass can be determined over oscillation frequencies modified in a predetermined manner. With a correct choice of the test parameters, e.g. the geometrical conditions in the measuring chamber, the dynamic moduli G' and G" have the character of absolute quantities, so that they are not dependent on specific rheometers or specific measuring devices. However, it is important for these measurements that the mass is only exposed to very low shear forces and correspondingly small reversible deformations, and that the measurements take place when the mass is in the rest state. During the operation of the kneader, with turbulent movement prevailing in the kneading chamber, it is not possible to determine with sufficient accuracy the dynamic parameters of a mass.

The problem of the invention is to provide a kneader of the aforementioned type, in which elastic and/or viscous parameters of the viscoelastic mass to be kneaded can be determined with an adequate precision, and also followed over time. In addition, a corresponding method for the rheometric analysis of a viscoelastic mass is to be provided.

SUMMARY OF THE INVENTION

According to the invention there is a test chamber, to which can be supplied from the kneading chamber a fraction of the mass, together with a preferably dynamically measuring rheometer for determining elastic and/or viscous parameters of the test fraction of the mass in the test chamber. Thus, according to the invention, during the kneading process a relatively small test fraction of 0 to 20% of the mass is temporarily branched off from the kneading chamber and supplied to the test chamber, where the test fraction is kept at rest and is in particular not subject to any turbulent movement. In this relative rest state the test fraction of the mass can in the aforementioned manner undergo a dynamic measurement with an oscillating movement, so that the storage modulus G' characterizing the elasticity and the loss modulus G" characterizing the dynamic viscosity can be very precisely determined. The rheometer can either be a CR (controlled rate) rheometer with preset rotation angle changes or a CS (controlled stress) rheometer with preset shear stresses.

It has proved advantageous not to keep the test chamber constantly available, but instead only to form it when the dynamic measurement is to be performed. According to the invention this is achieved in that the inner wall of the kneading chamber includes an adjustable wall part, and that the test chamber can be constructed by retracting the wall part. For performing the dynamic measurement the wall part is so adjusted that the test chamber adjacent to the kneading chamber is formed. The test fraction of the mass is then fed from the kneading chamber into the test chamber, and is in particular forced into it, and then the rheometer is introduced into the test chamber and the dynamic measurement carried out.

At the end of the measurement, the test fraction can be returned from the test chamber to the kneading chamber, and this preferably takes place in that the wall part is again moved back into its position forming a wall stage of the kneading chamber, so that the normal kneading process can be continued. If such a measurement is repeated at predetermined intervals, the kneading or mixing process on polymers and mixtures can also be followed over the kneading period, so as to reveal to what extent there is a change in the proportions of the viscous and elastic characteristics as a function of the test parameters, components of the mixture and mixing time.

Preferably and in per se known manner on the drive mechanism for the rotors is provided a further rheometer, making it possible by means of a measurement of the reaction torque on the driven rotor spindle to establish relative viscosity values of the mass in the kneading chamber. Thus, two independent rheometers are used, so as to analyze the rheological characteristics as a function of the measurement time of a viscoelastic mass, whilst presetting specific test parameters.

Kneaders are conventionally provided on the casing with a filling shaft in which is located a longitudinally movable piston by means of which the material components to be kneaded can be forced into the kneading chamber. The lower piston surface can form a wall part of the kneading chamber. According to the invention, preferably the adjustable wall part is formed by the lower piston surface, so that the test chamber can be formed by retracting the piston.

In order to engage the rheometer in a constructionally simple manner with the test fraction of the mass in the test chamber, the piston is preferably constructed as a hollow piston and the preferably dynamically measuring rheometer is integrated into the hollow piston. The rheometer can have a base plate terminating the bottom of the hollow piston and axially adjustable relative to said piston, whilst also being rotatable or oscillatable. Thus, the base plate on the one hand forms the lower piston surface and on the other hand forms the movable measuring plate of the rheometer.

The dynamically measuring rheometer comprises a rotary drive for the base plate, as well as a rotation angle sensor. As the base plate must also be axially displaceable relative to the hollow piston, a corresponding axial drive is also provided. Said components are placed in a rheometer casing, which is formed by a sectionwise extension of the hollow piston. The oscillating movement of the rheometer can also take place through an alternating movement of the axial drive.

The kneading chamber preferably contains two rotors rotated in opposite directions and whose rotation directions are reversible. By reversing the rotation directions the test fraction of the mass can be transferred from the kneading chamber into the test chamber.

With regards to the method, the set problem is solved in that a test fraction of the viscoelastic mass is supplied from the kneading chamber to a test chamber, where it is not exposed to a turbulent kneading movement and no longer participates in the kneading movement of the remaining mass, and the test fraction in the test chamber is dynamically investigated by means of a rheometer with respect to its elastic and/or viscous parameters, and the test fraction is subsequently returned to the kneading chamber.

Further features of the method according to the invention can be gathered from the above description of the kneader, and in particular the mass located in the kneading chamber is investigated with respect to its relative viscosity parameters by means of a further rheometer, which determines the reaction torque at the drive spindles of the rotors.

The rheometric measurement in the kneading chamber is performed during the kneading process, whilst the rheometric measurement in the test chamber can be performed either during a break or at least a slowing down of the kneading process, or also during the kneading process. The dynamic rheometric measurement in the test chamber and the rheometric kneading resistance measurement in the kneading chamber can be alternately successively performed several times.

BRIEF DESCRIPTION OF THE DRAWINGS

Further details and features of the invention can be gathered from the following description of an embodiment with reference to the attached drawings, wherein show.

DETAILED DESCRIPTION OF THE DRAWINGS

Figure 1:
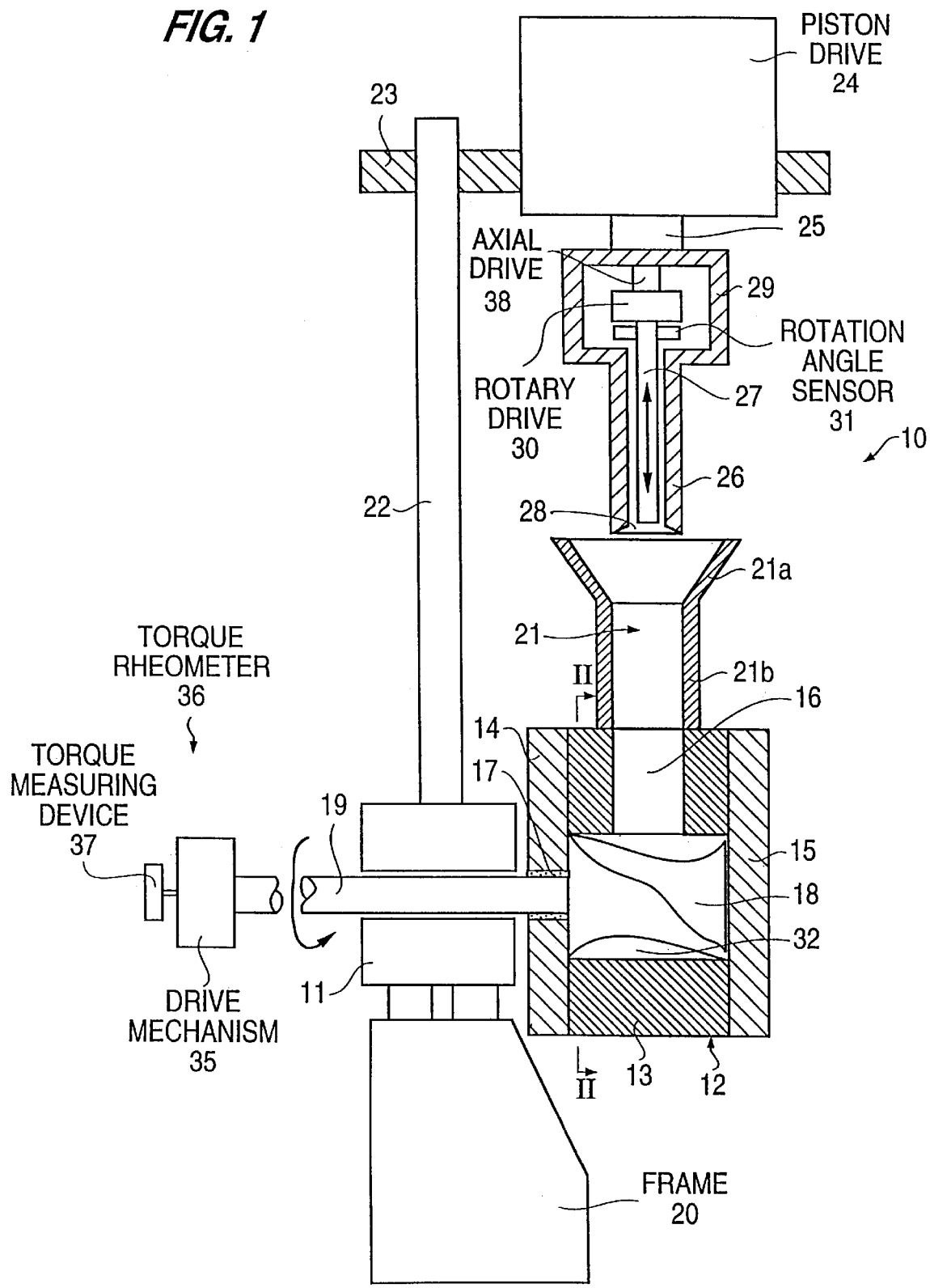
FIG. 1 A diagrammatic vertical section through a kneader according to the invention.

A kneader 10 shown in FIG. 1 constitutes an attachment part for a diagrammatically represented torque rheometer 36, which has a drive mechanism 35 and a measuring device 37 for determining a reaction torque.

Figure 2:
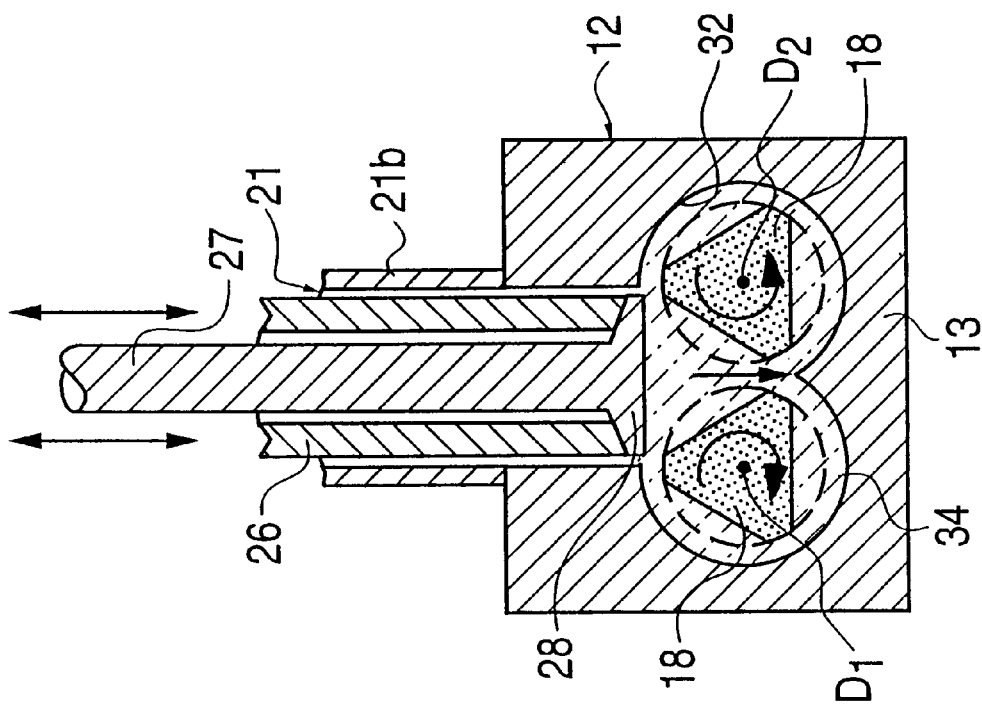
FIG. 2 Section II—II of FIG. 1.

The kneader 10 comprises a kneader stand 11 supported on a frame 20 and a bracket-like holder 22, 23, together with a casing 12, in whose interior is formed an elongated kneading chamber 32, whose cross-section is roughly double circular, i.e. in the form of an "8" (FIG. 2). The casing 12 is formed by a central part 13, terminally closed by in each case a front plate 14, 15. The kneading chamber 32 contains two rotors 18, which penetrate with a driven spindle 19 the rear front plate 14 and are rotatably mounted therein by means of a bushing 17. By means of the drive mechanism 35 of the torque rheometer 36, the rotors 18 can be driven in opposite directions about parallel, horizontal rotation axes $D_1$ and $D_2$, as indicated by the arrows in FIG. 2. Above the kneading chamber 32 the casing 12 in the central part 13 has an access opening 16, on which is mounted a diametrically circular sleeve 21b, accompanied by the formation of a filling shaft 21, which has at its upper end a funnel-shaped extension 21a and at its lower end the access opening 16. The filling shaft 21 extends substantially perpendicular to the rotation axes $D_1$, $D_2$ and issues above the same in the area between the rotors 18. Along the filling shaft 21 a piston 26 is axially displaceable into the access opening 16 and is connected by means of a piston rod 25 with a hydraulic or pneumatic drive or screw drive 24 mounted on the holder 23.

Figure 6:
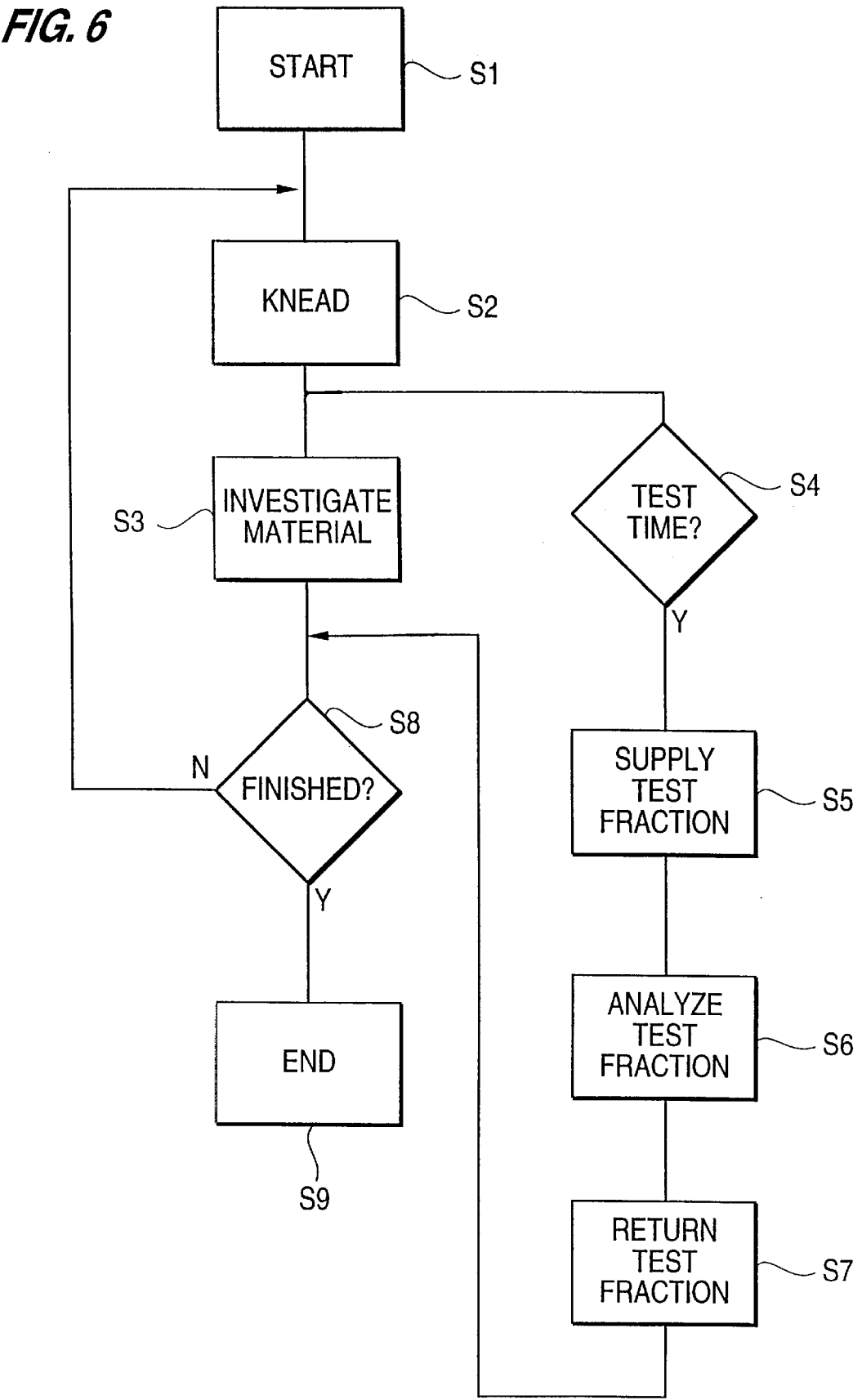
FIG. 6 A flow chart of an illustrative example of the method of the present invention.

The piston 26 is constructed as a hollow piston and has at its upper or rear end connected to the piston rod 25 an extension forming a rheometer casing 29. The lower end of the hollow piston 26 inserted in the filling shaft 21 is open and directly coverable by a base plate 28 which is located on the lower end of a shaft 27 penetrating the hollow piston 21. The rheometer casing 29 contains an axial drive 38 by means of which the shaft 27 and consequently the base plate 28 are axially adjustable relative to the hollow piston 26. In this way the base plate 28 can be moved from the lower end of the hollow piston 26 or tightly engaged therewith, and in the latter case it is positively in engagement in non-torsional manner with the hollow piston 26. The rheometer casing 29 also contains a rotary drive 30 for the shaft 27 and the base plate 28, as well as a rotation angle sensor 31 with which it is possible to precisely determine the oscillating rotary movement of the shaft 27. The base plate 28, rotary drive 30 and rotation angle sensor 31 form a dynamically measuring rheometer with which a test fraction of the mass to be kneaded can be exposed to precisely defined shear conditions, as will be described hereinafter. An illustrative example of the method of the present invention is shown in the flow chart of FIG. 6. The method starts in step S1.

For filling the kneading chamber 32 with the materials to be kneaded the piston 26 is completely removed from the filling shaft 21, so that the materials can be introduced through the latter into the kneading chamber 32. The piston 26 is then moved axially, so that it assumes the lower position shown in FIG. 2, where the lower piston surface, which is formed by the underside of the base plate 28, forms a wall section of the kneading chamber 32. In this position the base plate 28 is in non-torsional engagement with the hollow piston 26. The rotors 18 are then rotated in opposite directions and act on the mass 34 to be kneaded in the kneading chamber 32 in the area located between them. The rotors are rotated in the direction away from the piston 26 (according to FIG. 2 downwards, cf. arrow). (Step S2) During this first phase of the kneading process the resistance moment by which the mass 34 to be kneaded opposes the rotors 18 is determined by the torque rheometer 36 connected to the drive shaft 19 of the rotors 18. (Step S3)

Figure 3:
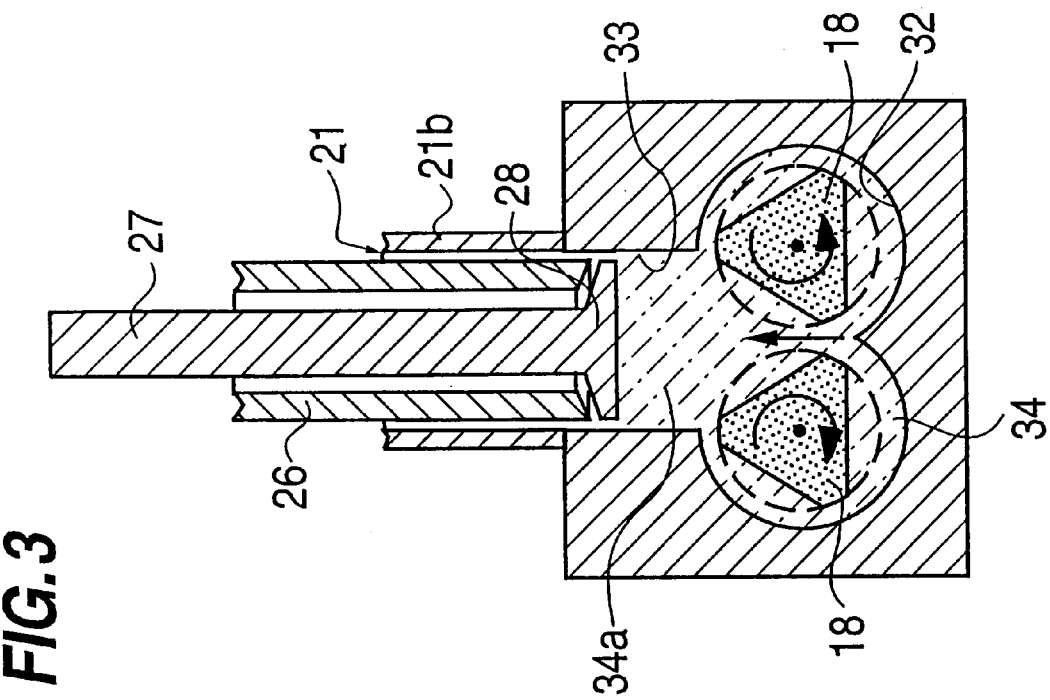
FIG. 3 A view according to FIG. 2 with the test chamber formed.

At the end of this first phase of the kneading process (Step S4) the rotation of the rotors 18 is stopped, and the piston 26 together with the base plate 28 is drawn back by a predetermined amount into the filling shaft 21, so that in the lower area of the filling shaft 21 or access opening 16 a test chamber 33 is formed. The shaft 27 with the base plate 28 is then moved axially by a small amount out of the hollow piston 26, so that the base plate 28 is freed from the non-torsional engagement with the hollow piston 26. The rotors 18 are then again rotated in opposition, but the rotation direction is reversed compared with the first phase of the kneading process. Thus, in the area located between them the rotors 18 exert on the mass 34 in the kneading chamber 32 a force directed towards the test chamber 33 (according to FIG. 3 upwards, cf. arrow), so that a test fraction 34a of the mass 34 is brought into the test chamber 33. (Step S5) Admittedly the test fraction 34a is held under pressure from below by the material movement in the kneading chamber, but it no longer participates in the circulating movement within said chamber 32, and in the test chamber 33 is roughly in a rest state, so that through an oscillating movement of the base plate 28 a rheometric, dynamic measurement can be performed on the test fraction 34a, in order to determine the moduli G' and G". (Step S6) At the end of this measurement the hollow piston 26 together with the base plate 28 is again moved axially into the filling shaft 21 until it assumes the position shown in FIG. 2, where the base plate 28 forms a wall section of the kneading chamber 32. The test fraction 34a is forced back out of the test chamber 33 into the kneading chamber 32. (Step S7) At the end, this second phase of the kneading process is continued corresponding to the first phase, in that once again the reaction torque is determined by means of the rheometer 36. This is again followed by the construction of the test chamber with the rheometric, dynamic measurement in accordance with the second phase. When the kneading is finished (Step S8), the method ends (Step S9).

Figure 4A:
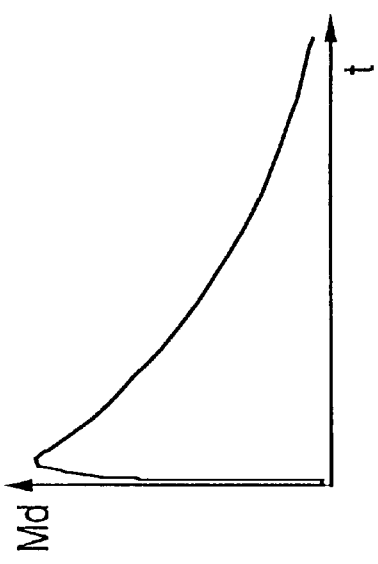
FIGS. 4a, 4b Curves obtained from the measured values of the kneader according to the invention.

By constantly alternating determination of the relative viscosity values by measuring the reaction torque on the driven rotor spindle (corresponding to the first phase) and the moduli G' and G" by a dynamic measurement using an oscillating movement of the base plate 28 (corresponding to the second phase), the diagrams shown in FIG. 4 can be obtained. The diagram according to FIG. 4a shows the decrease of the torque Md as a function of the kneading time t, the reaction torque being determined phasewise six times in the represented embodiment.

Figure 4B:
Figure 5A:
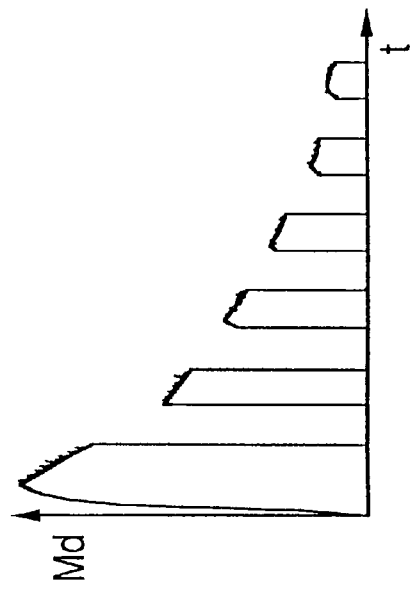
FIGS. 5a, 5b Curves obtained from comparison measurements.
Figure 5B:
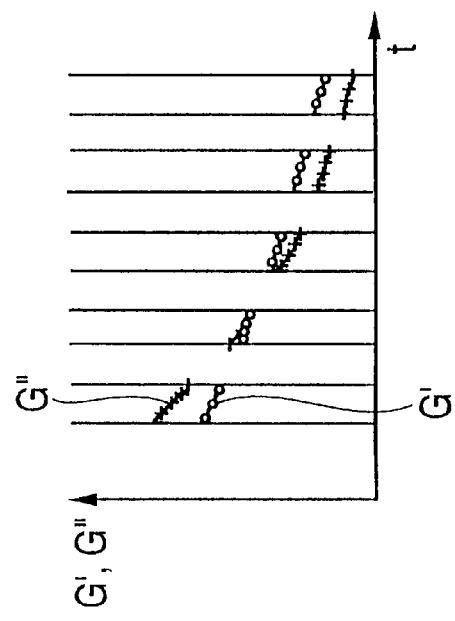

In the time portions between the reaction torque determination phases, the moduli G' and G" are determined in the indicated manner, as shown in FIG. 4b. The curved portions, considered over the total kneading time, give for both the decrease of the torque Md and the pattern of the moduli G' and G" curved, paths corresponding to those curves obtained in separate, continuous tests and whose results are shown for comparison purposes in FIGS. 5a and 5b.

I claim:

1. A kneader for kneading viscoelastic materials, comprising:
    a casing having interior walls defining a kneading chamber with an access opening, for receipt of materials to be kneaded;
    a pair of rotors within said kneading chamber for kneading the materials;
    at least a portion of one of the interior walls being movable between a forward position in which the movable wall portion cooperates with the interior walls to define the kneading chamber and a retracted position in which the movable wall portion cooperates with the access opening to define a test chamber extending from the kneading chamber for receipt of a test fraction of the materials; and
    a rheometer for determining elastic and/or viscous parameters of the lest fraction.

2. A kneader as claimed in claim 1, further comprising:
    a filling shaft connected to the access opening; and
    a piston positioned within the filling shaft and having the movable wall portion on a surface thereof, said piston being movable to move the movable wall portion between the forward position and the retracted position.

3. A kneader as claimed in claim 2, wherein the piston is hollow, and the rheometer is within the piston.

4. A kneader as claimed in claim 3, wherein:
    the rheometer is axially movable within the hollow piston between a first position and a second position; and
    the movable wall portion forms a portion of the rheometer, closing said end of the hollow piston when the rheometer is in the first position, and is rotationally movable in an oscillatory manner.

5. A kneader as claimed in claim 4, wherein the hollow piston includes a rheometer casing portion, and the kneader further includes an axial rheometer drive within the rheometer casing portion for moving the rheometer between the first and second positions, a rotary drive for moving the movable wall portion rotationally in an oscillatory manner, and a rotation angle sensor for sensing the rotational movement of the movable wall portion.

6. A kneader as claimed in claim 1, further comprising;
    a drive mechanism for driving the rotors;
    a further rheometer for determining the resistance of the kneaded material to the drive torque of the rotors.

7. A kneader as claimed in claim 1, wherein the rotors are positioned to push the test fraction into the test chamber.

8. A kneader as claimed in claim 7, further comprising a drive source for driving the rotors in a first direction, to knead the materials when the movable wall portion is in the forward position, and in a second direction, to push the test fraction into the test chamber when the movable wall portion is in the retracted position.

9. A method of rheometric analysis of a viscoelastic mass, comprising the steps of:
    (a) kneading the mass in a kneading chamber;
    (b) supplying a test fraction of the mass to a test chamber in which the test fraction is not exposed to kneading;
    (c) subjecting the test mass to rheometric analysis within the test chamber; and
    (d) returning the test mass to the kneading chamber.

10. A method as claimed in claim 9, further comprising:
    (e) investigating viscosity parameters of the test mass within the kneading chamber with a rheometer.

11. A method as claimed in claim 10, wherein during step (e), the mass without the test fraction is kneaded in the kneading chamber.

12. A method as claimed in claim 10,wherein step (c) and step (e) are performed alternately.

13. A method as claimed in claim 9, wherein during step (c), step (a) is interrupted.

14. A method as claimed in claim 9, wherein during step (c), the mass without the test fraction is kneaded in the kneading chamber.

* * * * *